United States Patent [19]

Wiezer et al.

[11] 4,239,891

[45] Dec. 16, 1980

[54] SUBSTITUTED PIPERIDINE HYDROXAMIDES, THEIR PREPARATION, AND THEIR USE AS LIGHT STABILIZERS

[75] Inventors: Hartmut Wiezer, Gersthofen; Gerhard Pfahler, Augsburg; Norbert Mayer, Gersthofen, all of Fed. Rep. of Germany

[73] Assignee: Hoechst Aktiengesellschaft, Fed. Rep. of Germany

[21] Appl. No.: 942,991

[22] Filed: Sep. 18, 1978

[30] Foreign Application Priority Data

Sep. 22, 1977 [DE] Fed. Rep. of Germany ....... 2742582

[51] Int. Cl.$^3$ .................... C07D 211/48; C08K 5/34
[52] U.S. Cl. ............... 546/242; 260/45.8 N; 260/45.8 NT; 260/45.85 B
[58] Field of Search ................ 260/45.8 NP; 546/242 (U.S. only)

[56] References Cited

U.S. PATENT DOCUMENTS

| | | | |
|---|---|---|---|
| 591,483 | 10/1897 | Merling | 260/293.88 |
| 2,778,825 | 1/1957 | Melamed | 106/176 |
| 3,534,048 | 10/1970 | Murayama et al. | 260/45.8 NP |
| 3,939,168 | 2/1976 | Cook | 260/45.8 NP |
| 4,046,736 | 9/1977 | Hardy | 260/45.8 NP |
| 4,052,361 | 10/1977 | Susi et al. | 260/45.8 NP |
| 4,055,536 | 10/1977 | Soma et al. | 260/45.8 NP |
| 4,064,102 | 12/1977 | Hillard et al. | 260/45.8 NP |
| 4,118,368 | 10/1978 | Soma et al. | 260/45.8 NP |

OTHER PUBLICATIONS

Noller, "Chemistry of Organic Compounds", 2nd Edition, 1957, p. 244.
Noller, "Chemistry of Organic Compounds", 3rd Edition, 1965, p. 276.
Wagner et al., "Synthetic Organic Chemistry", 1953, pp. 575 and 576.

*Primary Examiner*—Howard E. Schain
*Assistant Examiner*—R. A. White
*Attorney, Agent, or Firm*—Connolly and Hutz

[57] ABSTRACT

The invention provides novel derivatives of 2,2-dimethyl-6,6-dialkyl-4-hydroxy-4'-carbamoyl-piperidines which carry a substituent at the amide nitrogen atom, and optionally a further substituent at the ring nitrogen atom, and a process for preparing these compounds.

The products, optionally in the form of salts, are used for stabilizing thermoplastics against the damaging influence of light.

1 Claim, No Drawings

SUBSTITUTED PIPERIDINE HYDROXAMIDES, THEIR PREPARATION, AND THEIR USE AS LIGHT STABILIZERS

The invention provides novel derivatives of piperidine hydroxamides, the preparation thereof, and their use as stabilizers for synthetic polymers.

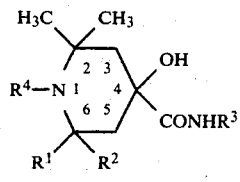
(I)

in which

R$^1$ and R$^2$, being identical or different, each are linear or branched alkyl radicals having from 1 to 12, preferably 1 to 6, carbon atoms, especially methyl groups, or R$^1$ and R$^2$ together with the carbon atom to which they are linked form an optionally methyl-substituted cyclopentane or cyclohexane ring or a 2,2,6,6-tetramethylpiperidine ring the carbon atom 4 of which is identical with the carbon atom 6 of the piperidine hydroxyamide ring, preferably the latter ring;

R$^3$ is a linear or branched alkyl radical having from 4 to 8 carbon atoms, preferably an isoalkyl radical having from 1 to 12 carbon atoms, especially a tert.-alkyl radical having from 1 to 8 carbon atoms the tertiary carbon atom of which is linked to the amide nitrogen, a hydroxymethylene group, or a benzyl radical optionally substitued by a C$_1$-C$_4$-alkyl radical, and R$^4$ is hydrogen, oxygen, hydroxyl, hydroxymethylene, or a C$_1$-C$_4$-alkyl group.

When the nitrogen atom 6 is substituted by H or alkyl, it has basic properties; the compounds may be present in these cases also in the form of salts of organic or inorganic acids.

Examples for R$^1$ and R$^2$ are methyl, ethyl, i-butyl, and for the case where R$^1$ and R$^2$ together with the carbon atom to which they are linked form a ring: cyclopentyl, cyclohexyl or 2,2,6,6-tetramethylpiperidyl.

Examples for R$^3$ are: tert.-butyl, 1,1-dimethylpropyl, 1-methyl-1-ethylpropyl, 1,1-diethylpropyl, 1,1,3,3-tetramethylbutyl, hydroxymethylene, benzyl.

Examples for R$^4$ are: hydrogen, hydroxymethylene, methyl, oxygen.

Examples of possible salts of compounds of the formula I are those with inorganic acids such as phosphates, phosphites, chlorides, sulfates, or salts with organic monoand polycarboxylic acids such as acetates, laurates, stearates, succinates, sebacates, maleates, citrates, tartrates, oxalates, benzoates, sulfonates or phosphonates etc..

Examples of compounds of the formula I are the following:

2,2,6,6-tetramethyl-4-hydroxy-4-tert.-butylcarbamoyl piperidine.

2,2,6,6-tetramethyl-4-hydroxy-4-(1,1-dimethylpropyl)-carbamoyl piperidine, 2,2,6,6-tetramethyl-4-hydroxy-4-(1-methyl-1-ethylpropyl)-carbamoyl piperidine, 2,2,6,6-tetramethyl-4-hydroxy-4-hydroxymethylene-carbamoyl piperidine, 1-hydroxymethylene-2,2,6,6-tetramethyl-4-hydroxy-4-hydroxymethylene-carbamoyl piperidine.

The novel compounds of formula I where both the radicals R$^3$ and R$^4$ are not hydroxymethylene groups are obtained by reaction of 2,2-dimethyl-6,6-dialkyl-4-hydroxy-4-cyanopiperidine with an alcohol, optionally also with an olefin. The reaction proceeds according to the following scheme (a), in which R$^1$, R$^2$ and R$^3$ are as defined above.

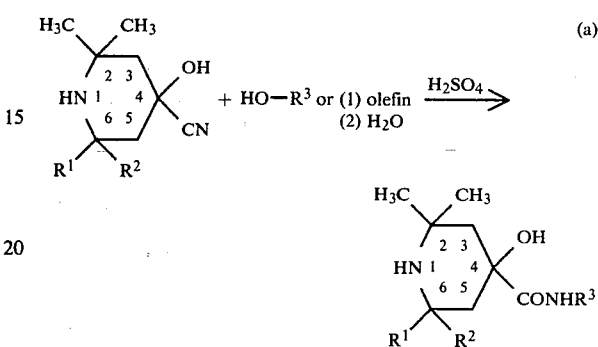

In this case, the reaction is carried out as follows: the piperidine cyanohydrine, either in excess of the alcohol or together with the equimolar amount of the alcohol or olefin is introduced into the reactor in a suitable organic solvent such as glacial acetic acid, the double molar amount of sulfuric acid is added dropwise, and the reaction is allowed to proceed at a temperature of from 30° to 120° C., preferably 50° to 100° C., and especially 60° to 80° C. The reaction time is from 1 to 20, preferably 2 to 10, hours. When an olefin is used, an at least equimolar amount of water has to be added after the reaction is complete. The hydrosulfate precipitated in the course of the reaction (sometimes it has to be precipitated by adding a solvent such as acetone) is converted to the free base by treatment in aqueous solution with a base such as ammonia or NaOH, and in this form it can be filtered off as solid matter from the aqueous phase.

Compounds where R$^3$ is a hydroxymethylene group are obtained according to the reaction scheme (b)

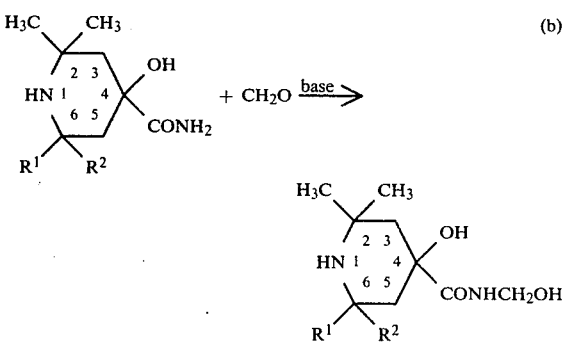

by reacting an alpha-hydroxy-amide unsubstituted at the amide group, which can be easily obtained for example according to German Offenlegungsschrift No. 2,602,673, with formaldehyde, in aqueous solution with addition of a strong base, for example K$_2$CO$_3$, as catalyst, at temperatures of from 20° to 100° C., preferably 40° to 80° C. When the double amount of formaldehyde is used, the amine group of the piperidine ring, too, is substituted by hydroxymethylene.

The compounds where $R^4$ is alkyl are prepared by reacting the compound where $R^4$ is hydrogen with an alkyl halide in the presence of a base.

The novel piperidine hydroxamides are excellently suitable for stabilizing synthetic polymers against the decomposing effect of light and heat.

By synthetic polymers, there are to be understood in this connection halogen-free and halogen-containing homo- and copolymers, in particular homopolymers of olefins, dienes and styrene, for example polyethylene of low and high density, polypropylene, polystyrene, polybutadiene and polyisoprene, copolymers of olefins, dienes, and styrene with one another or with other olefinically unsaturated monomers, such as ethylene-propylene copolymers, ethylene-butene copolymers, styrene-butadiene copolymers, ethylene-vinyl acetate copolymers and acrylonitrile-butadiene-styrene copolymers, homopolymers of vinyl chloride and vinylidene chloride and copolymers of these monomers with one another and with other olefinically unsaturated monomers. There are also to be included polyurethanes, polyacetals, polyesters, polyamides, polyacrylates, and epoxy resins. Preference is given to poly-α-olefins, such as polyethylenes and especially polypropylenes, as well as to the polymers of vinyl chloride.

It was surprising and not to be expected that the products of the invention are considerably superior with respect to their light stabilizing effect to the compounds having comparable structural characteristics, described in U.S. Pat. Nos. 3,334,103 and 3,534,048, French Pat. Nos. 1,360,030 and 2,204,630, Japanese Pat. No. 7,131,743, and German Offenlegungschrift No. 1,695,738. For, since the structural modifications were supposed to be rather insignificant, it could be assumed that the effect of the compounds of the invention would be about the same.

The stabilizers according to the invention are incorporated into the polymer compositions according to methods that are generally common. Alternatively, it is also possible to mix a solution, suspension or emulsion of the stabilizer directly with the polymer, or with a solution, suspension or emulsion of the same, and to eliminate the solvent thereafter.

The stabilizers of the invention may be used alone or in admixture with one or several of the stabilizers which are common in the processing of plastic materials, such as antioxidants on the basis of phenol and sulfide, UV-absorbers and light protecting agents, phosphite stabilizers, metal compounds, epoxy stabilizers and polyhydric alcohols. In the plastic compositions to be stabilized there may also be present flame-proofing agents and pigments, dyestuffs, antistatic agents and fillers, such as glass fibers.

Examples for appropriate antioxidants are those of the type of the sterically hindered phenols, such as 2,6-di-t.-butyl-p-cresol, 2,6-di-octadecyl-p-cresol, 4,4'-butylidene-bis-(2,6-di-t.-butyl-phenol), 4,4'-thio-bis-(2-t.-butyl-5-methyl-phenol), phenolic triazine compounds, thiodipropionic acid esters of fatty alcohols, dioctadecyl sulfide and -disulfide.

The UV-absorbers and light protecting agents include, for example, 2-(2'-hydroxyphenyl)-benzotriazoles, such as 2-(2'-hydroxy-5'-methylphenyl)-benzotriazole, 2-hydroxybenzophenones, such as 2-hydroxy-4-octoxy-benzophenone, stabilizers of the group of the salicylates, such as octylphenyl salicylate, nickel chelates, oxalic acid diamides and sterically hindered piperidine compounds.

As phosphites there are to be mentioned trisnonylphenyl phosphite, trislauryl phosphite or esters of pentaerythritol phosphite.

By metal compounds known as stabilizers there are to be understood: Calcium, barium, strontium, zinc, cadmium, magnesium, aluminum and lead soaps of aliphatic carboxylic acids or hydroxycarboxylic acids having from about 12 to 32 carbon atoms, salts of the aforesaid metals with aromatic carboxylic acids, such as benzoates or salicylates, and (alkyl-)phenolates of these metals, and also organo-tin compounds such as, for example, dialkyltin thioglycolates and carboxylates.

Known epoxy stabilizers are, for example, epoxidized higher fatty acids, such as epoxidized soy bean oil, tall oil, linseed oil or epoxidized butyl oleate, and also epoxides of long-chain olefins.

Polyhydric alcohols may be, for example, pentaerythritol, trimethylolpropane, sorbitol or mannitol, i.e. preferably alcohols having 5 or 6 carbon atoms and from 3 to 6 OH-groups.

An effective stabilizer combination for poly- -olefins such as, for example, high, medium and low pressure polymers of $C_2$- to $C_4$- -olefins, especially polyethylene and polypropylene or copolymers of such -olefins, consists, calculated on 100 parts by weight of polymer, for example, of from 0.01 to 5 parts by weight of one of the compounds to be used in accordance with the invention, of from 0.05 to 5 parts by weight of a phenolic stabilizer, optionally of from 0.01 to 5 parts by weight of a sulfur-containing costabilizer, and optionally of from 0.01 to 3 parts by weight of a basic or neutral metal soap such as, for example, calcium stearate or zinc stearate, and optionally of from 0.1 to 5 parts by weight of a phosphite and optionally of from 0.01 to 5 parts by weight of a known UV-stabilizer of the group of alkoxy-hydroxy-benzophenones, hydroxyphenyl-benzotriazoles, benzylidene-malonic acid-mononitrile esters or the so called quenchers, such as nickel chelates.

The following Examples serve to illustrate the invention. The structures of the compounds were determined by nuclear resonance spectroscopy.

EXAMPLE 1

2,2,6,6-Tetramethyl-4-hydroxy-4-hydroxymethylene-carbamoyl piperidine 116 g 2,2,6,6-Tetramethyl-4-hydroxy-4-carbamoyl piperidine in 70 ml water are introduced into the reactor, and 45 g 40% formaldehyde solution and 2 g $K_2CO_3$ are added, the mixture is heated to 80° C. within 2 hours, and agitation is then continued for 1 hour at this temperature. Subsequently, the reaction batch is concentrated to ¼ of its volume, the solids are suction-filtered, and the product is dried. Yield 66 g, m.p. 92° C.

EXAMPLE 2

1-Hydroxymethylene-2,2,6,6-tetramethyl-4-hydroxy-4-hydroxymethylene-carbamoyl piperidine 20 g 2,2,6,6-Tetramethyl-4-hydroxy-4-carbamoyl piperidine in 20 ml water are introduced into the reactor. 30 g 40% formaldehyde solution and 0.5 g $K_2CO_3$ are added, and the mixture is then heated with agitation to 100° C. within 4 hours. After having distilled off the water, the residue is stirred with acetone, which causes the intended product to precipitate. Yield 16 g, m.p. 164° C.

EXAMPLE 3

2,2,6,6-Tetramethyl-4-hydroxy-4-tert.-butylcarbamoyl piperidine 54.6 g 2,2,6,6-Tetramethyl-4-hydroxy-4-cyanopiperidine together with 45 g tert.-butanol in 200 ml glacial acetic acid are introduced into the reactor. Subsequently, 60 g concentrated sulfuric acid are added dropwise with agitation, and agitation is continued for 2 hours at 70° C., thus forming a precipitate which is filtered off and dissolved in water. On alkalization with NaOH, the product precipitates, it is suction-filtered and recrystallized from ethyl acetate. Yield 44 g, m.p. 134°–136° C.

EXAMPLE 4

2,2,6,6-Tetramethyl-4-hydroxy-4-(1,1-dimethylpropylcarbamoyl)-piperidine is prepared according to Example 3, but with the use of 2-methyl-butanol-2 instead of tert.-butanol. The product is recrystallized from heptane. Yield 55%, m.p. 115°–117° C.

EXAMPLE 5

2,2,6,6-Tetramethyl-4-hydroxy-4-(1-methyl-1-ethyl-propylcarbamoyl)-piperidine 36.4 g 2,2,6,6-Tetramethyl-4-hydroxy-cyanopiperidine in 100 ml 3-methylpentanol-3 are introduced into the reactor. 40 g concentrated sulfuric acid are added dropwise with agitation, and the batch is then heated for 1 hour at 70° C. The precipitate is suction-filtered and treated in water with NaOH. The free base is obtained by filtration, and recrystallization is carried out in ethyl acetate. Yield 38 g, m.p. 127°–129° C.

EXAMPLE 6

This example demonstrates the light stabilizing action of the compounds of the invention when applying them to a poly-alpha-olefin.

100 parts by weight of polypropylene having a melt flow index $i_5$ of about 6 g/10 min. (determined according to ASTM D 1238-62 T) and a density of 0.96, were mixed with 0.1 part by weight of pentaerythrityl-tetrakis-[3-(3,5-di-tert.-butyl-4-hydroxyphenyl)-propionate], 0.2 part by weight of calcium stearate and 0.1 part by weight of the stabilizer of the invention to be tested. In order to obtain a uniform distribution on the polymer grain, the stabilizers were dissolved in a solvent, and the solution was added dropwise with agitation to the polypropylene powder, while simultaneous radiation by means of an IR lamp ensured substantial evaporation of the solvent. After about 20 minutes, the calcium stearate was added, and the batch was mixed for a further 10 minutes. The solvent remainder was removed by drying in a drying cabinet at 50° C. for 120 minutes.

On a Windsor injection molding machine type SP 50, plates having the dimensions of 60×60×1 mm were molded at 250° C. from the above stabilized plastic mixture, and test specimens according to German Industrial Standard DIN 53 455, form 3, in a scale reduced at a 1:3 ratio, were cut from these plates. The test specimens required as comparative samples were prepared and formed in analogous manner, while omitting either the stabilizer to be tested (Test g) or using known light stabilizers (Tests c to f).

The stability to light was tested according to German Industrial Standard DIN 53 387 (accelerated test of weathering-resistance) using a (R)Xenotest 450 apparatus of the company Original Hanau Quarzlampen GmbH and the filter combination 6 IR+1 UV. During the time of exposure, the blackpanel temperature was 43°±1° C., and the relative atmospheric moisture in the test chamber was 70%±1%. Fresh air was passed through the test chamber for 5 minutes every 2 hours. After a defined time of exposure, the elongation at break was determined on a tensile testing machine of the Instron company at a draw-off speed of 5 cm/min. The results are listed in the following Table.

The stabilizing factor follows from the ratio of radiation time of the stabilized test specimens to the radiation time of the non-stabilized test specimens; the radiation being continued in all cases until the elongation at break had dropped to half the starting value.

As results from the Table, the stabilizing effect of the compounds of the invention is better than that of a benzophenone or benzotriazole stabilizer. It is also better than that of 2,2,6,6-tetramethyl-4-hydroxy-4-cyanopiperidine (U.S. Pat. No. 3,334,103, French Pat. No. 1,360,030 and Japanese Pat. No. 71,31,733) and of 2,2,6,6-tetramethyl-4-hydroxy-iminopiperidine (Japanese Pat. No. 71,31,733), of which the latter one moreover causes the polymer composition to become turbid.

| Test No. | Stabilizer acc. to Example | Stabilizing factor |
|---|---|---|
| (a) | 2 | >5 |
| (b) | 3 | >5 |
| (c) | Benzophenone stabilizer[1] | <2.5 |
| (d) | Benzotriazole stabilizer[2] | <2.5 |
| (e) | 2,2,6,6-tetramethyl-4-hydroxy-iminopiperidine | 3.0 |
| (f) | 2,2,6,6-tetramethyl-4-hydroxy-4-cyano-piperidine | 2.8 |
| (g) | Control (without stabilizer) | 1 |

[1]2-Hydroxy-4-n-octyloxybenzophenone
[2]2-(2-Hydroxy-3',5'-di-tert.-butylphenyl)-5-chlorobenzotriazole

What is claimed is:

1. A process for the preparation of piperidine hydroxyamides of the formula

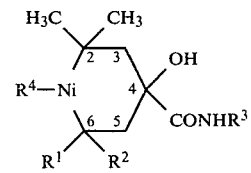

in which
 $R^1$ and $R^2$ are methyl;
 $R^3$ is tertiary alkyl of 4–8 carbons; and
 $R^4$ is hydrogen or alkyl of 1–4 carbons,
which comprises reacting 2,2,6,6-tetramethyl-4-hydroxy-4-cyanopiperidine in an organic solvent with a tertiary alcohol of 4 to 8 carbons or an olefin of the same number of carbons, with addition of sulfuric acid as catalyst, in which process when an olefin is used at least an equimolar amount of water is added after the reaction is complete.

* * * * *